United States Patent [19]

Das

[11] Patent Number: 4,972,287

[45] Date of Patent: Nov. 20, 1990

[54] HAVING A SOLENOIDAL ENERGIZING COIL

[75] Inventor: Shyam Chandra Das, Acton, Mass.

[73] Assignee: Digital Equipment Corp.

[21] Appl. No.: 449,133

[22] Filed: Dec. 8, 1989

Related U.S. Application Data

[60] Continuation of Ser. No. 370,160, Jun. 21, 1989, abandoned, which is a continuation of Ser. No. 233,321, Aug. 17, 1988, abandoned, which is a division of Ser. No. 69,428, Jul. 1, 1987, abandoned.

[51] Int. Cl.$^5$ ............................. G11B 5/17; G11B 5/31
[52] U.S. Cl. ..................................... 360/126; 360/123
[58] Field of Search .............................. 360/123, 126

[56] References Cited

U.S. PATENT DOCUMENTS

| 3,634,632 | 1/1972 | Watson | 360/123 |
|---|---|---|---|
| 3,662,119 | 5/1972 | Romankiw et al. | 360/123 |
| 3,903,586 | 9/1975 | Whetstone | 29/603 |
| 4,251,910 | 2/1981 | Griffith | 29/603 |
| 4,416,056 | 11/1988 | Takahashi | 29/603 |
| 4,511,942 | 4/1985 | Valstyn | 360/126 |
| 4,639,289 | 1/1987 | Lazzari | 360/123 |
| 4,644,130 | 1/1987 | Bachmann | 219/121 LJ |
| 4,644,432 | 2/1987 | Heim | 360/123 |
| 4,652,956 | 3/1987 | Schewe | 360/123 |
| 4,652,957 | 3/1987 | Schewe et al. | 360/125 |
| 4,672,493 | 6/1987 | Schewe | 360/125 |
| 4,684,438 | 8/1987 | Lazzari | 360/123 |
| 4,727,643 | 3/1988 | Schewe et al. | 29/603 |

FOREIGN PATENT DOCUMENTS

| 3501810 | 7/1986 | Fed. Rep. of Germany . |
|---|---|---|
| 1107665 | 1/1956 | France . |
| 55-45192 | 7/1980 | Japan . |
| 59-119522 | 7/1984 | Japan . |
| 60-66312 | 4/1985 | Japan . |
| 60-247815 | 12/1985 | Japan . |
| 61-18871 | 3/1986 | Japan . |
| 61-95792 | 5/1986 | Japan . |
| 61-284814 | 12/1986 | Japan . |
| 7950D5 | 2/1981 | U.S.S.R. . |
| 1216905 | 12/1970 | United Kingdom . |

OTHER PUBLICATIONS

Albert et al., "Method of Forming a Probe-Type Head for Vertical Recording", IBM Technical Disclosure Bulletin, vol. 23, No. 11, Apr. 1981, p. 5097.

Primary Examiner—Robert S. Tupper
Attorney, Agent, or Firm—Fish & Richardson

[57] ABSTRACT

A new read/write head for use in a mass storage device in a digital data processing system. The head is a thin-film head having a solenoidal coil around one or both of the pole pieces. Sets of planar conductive traces are formed on planar layers of insulating material on opposing sides of a pole piece, with vias connecting the ends of selected traces to thereby form a solenoidal coil around the pole piece.

16 Claims, 1 Drawing Sheet

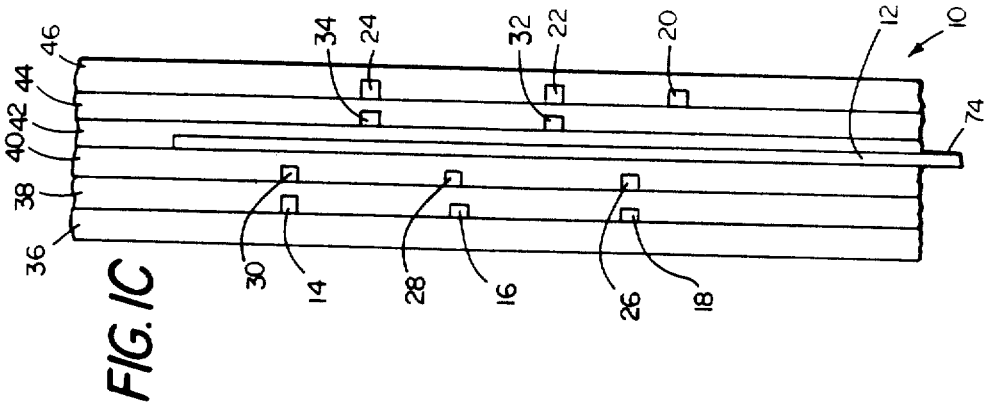
FIG. IC
FIG. IB
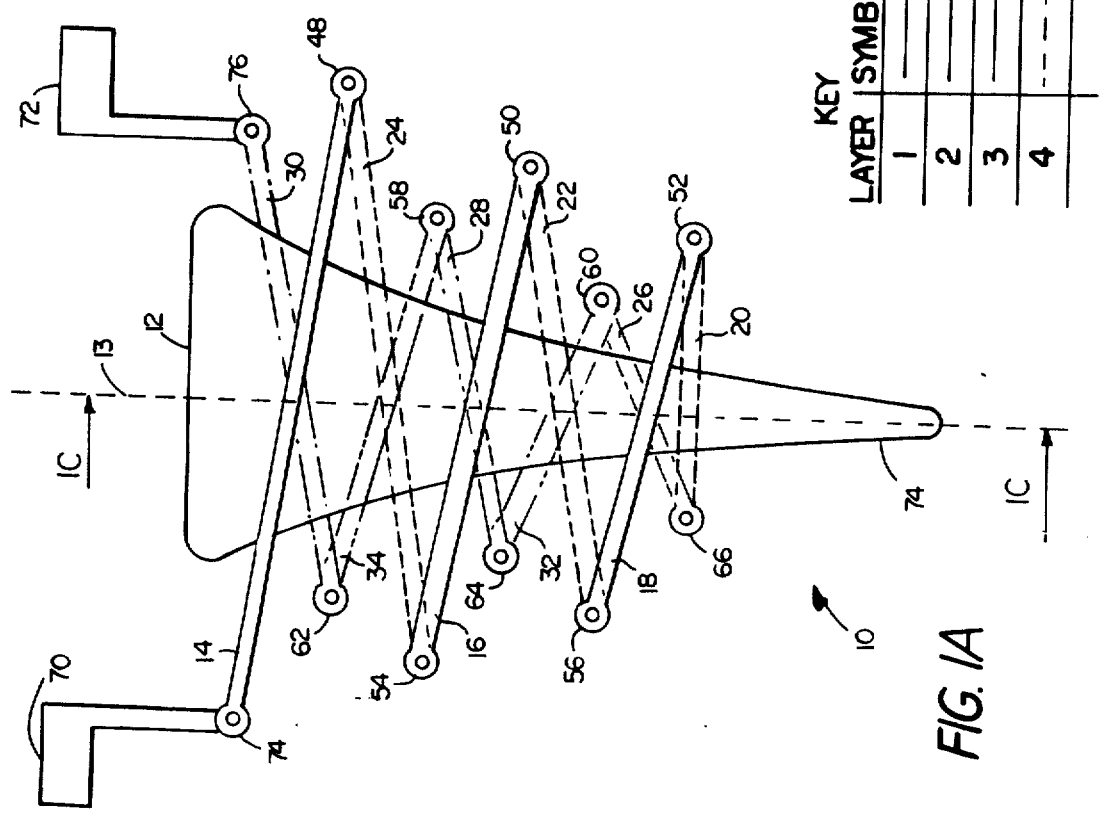
FIG. IA

HAVING A SOLENOIDAL ENERGIZING COIL

This is a continuation of copending application Ser. No. 07/370,160 filed on Jun. 21, 1989 which is a continuation of application Ser. No. 233,321, filed on Aug. 17, 1988, now abandoned, which is a divisional of Ser. No. 069,408, filed Jul. 1, 1987.

CROSS-REFERENCE TO RELATED PATENT APPLICATION

U.S. patent application Ser. No. 894,784, filed Aug. 8, 1986, in the name of Shyam Chandra Das, for Microlithographic Technique Using Laser For Fabrication Of Electronic Components And The Like, which is incorporated herein by reference.

BACKGROUND OF THE INVENTION

1. Field of the Invention

The invention relates generally to the field of read/write heads for use in mass storage devices for digital data processing systems, and more particularly to such heads manufactured by thin film techniques. The invention provides a new thin film head which incorporates a solenoidal energizing coil, and a method of fabricating the new head.

2. Description of the Prior Art

A typical modern digital data processing system comprises a hierarchy of memory devices, including a semiconductor main memory of relatively small capacity, and one or more mass storage devices, which have much greater capacity than the main memory, but which are also relatively much slower. The mass storage devices provide a back-up store for data which is in the main memory, and also for the voluminous amounts of data which will not fit into main memory but which can be called upon by the processor when it is needed. A processor typically only obtains information directly from the main memory, and so, when it needs information which is only in a mass storage device, it enables the mass storage device to copy the information to the main memory. Some time later, after it has processed the information, the processor enables the processed information to be stored in the mass storage device. This frees up storage in the main memory so that other information may be stored there.

Typical mass storage devices store information on magnetic disks, the information being recorded in the form of transitions in magnetic flux in the magnetic media generated by a read/write head. The information is organized into a plurality of tracks, each a selected radial distance from the center of the disk, and each track is divided into a plurality of sectors, with each sector subtending a predetermined angular portion of the disk. The read/write head is suspended from an arm, which is moved generally radially over the disk surface in a "seek" operation to bring the read/write head into registration with a selected disk track. The disk is rotated in a "search" operation to bring the sector containing the desired information into angular registration with the read/write head, which reads the information contained in the sector, or writes information on the magnetic medium in the sector.

Originally, read/write heads were generally toroidal in shape with a cut or gap, with the ends of the toroid at the gap being pole pieces. A wire coil was wound around the toroid and is energized to generate magnetic flux. The flux diverges between the pole pieces and impinges on the magnetic material of the disk. The density with which data may be written is directly related to the number of flux transitions, or changes in flux direction, which the heads may provide per unit of time. Since these heads have a relatively high electrical inductance, to achieve a satisfactory rate of flux transitions, expensive driving circuitry is required. Furthermore, the high inductance results in increased "ringing", in which a signal, at a sharp transition, tends to fluctuate about the desired signal level. Too much ringing leads to uncertainty in the signal level for too long a time, which requires slowing down the system.

More recently, thin film read/write heads have been developed which have much lower inductance than conventional read/write heads. Thin film read/write heads are fabricated by means of lithographic techniques that are generally similar to the techniques that are used in making integrated circuit chips. In such techniques, a planar pole piece is first formed and covered with an insulating material. A coil is then formed on the insulating material in the shape of a planar spiral over part of the pole piece, an insulating material is deposited over the spiral, and another pole piece is formed on top of the insulating material.

However, because the coil, of a typical thin film read/write head has a planar spiral shape, a relatively long conductor is required to provide the number of turns in the coil that is required to generate the desired magnetic field during the write operation, or to intercept the magnetic field sensed by the head during a read operation. Since, in a planar spiral, the length of the conductor increases faster than the number of turns, the long spiral conductor results in a relatively large resistance, which, in turn, results in generation of a significant amount of heat. The increase in the resistance of the coil also results in a concomitant increase in the noise of the signal during the reading operation.

Furthermore, when the coil has a spiral shape, the mutual inductance between turns also increases faster than the number of turns, and so a planar coil having a sufficient number of turns also has a relatively high inductance. The high inductance results in a relatively low effective resonant frequency, which, in turn, increases the amount of undesirable ringing that can occur in a signal applied to the coil. In addition, since the coil has a relatively high inductance, a high driving voltage is required during a write operation to provide the necessary write current.

U.S. Pat. No. 3,662,119, entitled Thin Film Magnetic Transducer Head, issued May 9, 1972, to L. Romankiw, et al., discloses a thin film head having a solenoidal coil formed around both pole pieces in the head to provide both a supply and a return path for electrical current which energizes the coil. The coil is formed in one layer around each pole piece using a complex fabrication method. Since coil layers are required around both pole pieces, the coil is not suitable for use in connection with vertical recording techniques now being developed, in which data is recorded vertically rather than horizontally on a disk surface.

SUMMARY OF THE INVENTION

The invention provides a new and improved thin film read/write head for a disk storage unit in a digital data processing system, in which the energizing coil is in the form of a solenoid around at least one of the pole pieces, and a method of fabricating the head.

In brief, the new head includes a pair of planar pole pieces. A solenoidal coil is formed around at least one of the pole pieces, the solenoid coil being in the shape of several series of planar traces of conductive material on opposing sides of the pole piece, spaced apart from the pole piece by planar layers of insulating material. The traces are in a generally skewed direction to the axis of the pole piece. The ends of several of the traces on the opposing sides of the pole piece overlay each other and are connected together through vias to form a coil layer effectively forming a continuous circuit with planar traces interconnected by vias. When current is applied, a magnetic field is generated in the pole piece. After the coil is formed around the one pole piece, the second pole piece may be formed on one side thereof. The skewing of the traces permits the applied electrical current to have a direction of movement along the axis of the pole piece while traveling around the pole piece through the traces and vias.

In a refinement, the coil may comprise two layers of traces on each side of the pole piece to essentially form two layers of coils, an interior layer and an exterior layer, around the pole piece. The two coil layers effectively allow a return path for current applied to the head through one of the coil layers. The interior coil is formed from traces which are, on each side of the pole piece, skewed in opposite directions to the axis from the outer coil layer, with the traces forming the interior coil being somewhat shorter than the traces of the outer coil layer and closer to the pole piece. The ends of the traces forming the interior coil also overlay each other and are connected together through vias. The shorter traces result in the formation of a coil which is interior of the other coil. The outer and inner coils are connected together at one end thereof.

In the method of fabricating the new head, a planar base is first formed and a series of conductive traces are formed thereon in a generally parallel direction which is skewed with respect to the direction selected for the axis of the pole piece which will be formed later. The traces may be formed by known photolithographic methods. A second insulating layer is then deposited thereover. If a second coil layer is to be formed, a second layer of traces is formed on the second insulating layer skewed in the opposite direction, from the direction of the first layer of traces, with respect to the selected direction for the pole piece axis.

After the second coil layer is formed, a third insulating layer is formed and a pole piece is formed, again by photolithographic techniques. A fourth insulating layer is formed and a third set of traces is formed, which is associated with the interior coil. The ends of the third layer of traces generally overlay a number of the ends of the second layer of traces, and the traces are generally skewed in the opposite direction, with respect to the axis of the pole piece, as the second layer of traces. During this process, vias are formed between the ends of the second and third sets of traces and conductive material is deposited in the vias completing the interior coil. The vias may be formed by the method described in the above-referenced U.S. patent application Ser. No.

After the interior coil is completed, a fifth insulating layer is deposited and a fourth set of traces is formed which is associated with the exterior coil. The ends of the fourth set of traces generally overly the ends of the first set of traces, except for an end which overlies and end of the second set of traces. Vias are formed to the underlying ends and conductive material is deposited therein. This completes the outer coil and the connection to the interior coil.

BRIEF DESCRIPTION OF THE DRAWINGS

This invention is pointed out with particularity in the appended claims. The above and further advantages of this invention may be better understood by referring to the following description taken in conjunction with the accompanying drawings, in which:

FIG. 1A is a view representing a schematic layout of the various traces and the pole piece forming part of a read/write head constructed in accordance with this invention, FIG. 1B is a table that is useful in understanding FIG. 1A; and FIG. 1C is a schematic side sectional view, taken along axis 1C—1C, of the portion of the head illustrated schematically in FIG. 1A.

DETAILED DESCRIPTION OF AN ILLUSTRATIVE EMBODIMENT

With reference to the Figures, a new read/write head 10 constructed in accordance with the invention includes a pole piece 12 and a plurality of traces of conductive material formed on layers of insulating material such as hard baked photoresist, silicon dioxide ($SiO_2$) and alumina ($Al_2O_3$). The traces are formed at predetermined angles with respect to a longitudinal axis 13 of the pole piece 12 and interconnected by conductive material deposited in vias in the conductive material as described below. The configuration of the conductive traces, that is, their placement and orientation relative to each other and to the pole piece 12, and of the vias, is selected so that they form a solenoidal coil around the pole piece.

The head 10 includes four layers of conductive traces formed on planar layers of insulating material, with two layers being disposed under the pole piece 12 and two layers being disposed above pole piece 12. In particular, two of the layers of traces comprise a lower, or first, trace layer including three traces 14, 16 and 18 and an upper, or fourth, trace layer also including three traces 20, 22 and 24. As shown in FIG. 1B, the traces 14, 16, and 18 are all depicted in FIG. 1A by means of solid lines, with each pair of solid lines representing one trace. Similarly, the traces 20, 22 and 24 are all depicted in FIG. 1A by means of dashed lines with each pair of dashed lines representing one trace.

The other two layers of traces include a second trace layer, comprising three traces 26, 28 and 30 situated between the first trace layer and the pole piece 12, and a third trace layer comprising two traces 32 and 34 situated between the fourth (upper) trace layer and the pole piece 12. As shown in FIG. 1B, the traces 26, 28 and 30 are all depicted in FIG. 1A by a dashed line having alternating long and short dashes, and traces 32 and 34 are depicted in FIG. 1A by a dashed line having alternating one long and two short dashes.

As shown in FIG. 1C, the pole piece 12 and all of the traces are formed on and embedded in layers of insulating material. Six layers of insulating material are depicted in FIG. 1C, namely, layers 36, 38, 40, 42, 44 and 46. As explained below in greater detail, after insulating layer 36 and traces 14, 16 and 18 are formed, the sequential insulating layers 38, 40, 42, and 44 are deposited and the respective traces or pole piece 12 are formed thereon. The ends of the traces of the various trace layers are connected together appropriately, as described below, to form a solenoidal coil. In particular, ends of selected pairs of traces overly each other, and the overlying ends are connected together through the vias. After the upper trace layer, that is, traces 20, 22 and 24, has been formed, and all of the connections through the vias have been formed, an insulating layer 46 is applied thereto to cover the traces. Thereafter, a second pole piece (not shown) may be formed on the head 10 as appropriate.

As has been mentioned, the traces are interconnected by appropriate vias which are formed through the insulating layers between the ends of the traces. These interconnections are such as to form a continuous circuit, with the traces and vias cooperating to effectively form a coiled electrical path around pole piece 12 from the upper end (as shown in FIG. 1) to the tip 74. One such via, namely via 48, connects the right end (as shown in FIG. 1A) of trace 14 in the lower trace layer, to the right end of trace 24 in the upper trace layer. Similarly, vias 50 and 52 interconnect the respective right ends of the other traces 16 and 22, and 18 and 20, in the lower and upper trace layers. Similar vias 54 and 56 interconnect the left ends of respective pairs of traces 16 and 24, 18 and 22, between the first (lowest) and fourth (uppermost) trace layers. The result is a solenoid coil around pole piece 12 which extends from the leftmost end of trace 14 near the top of pole piece 12 (as shown in FIG. 1A) to the leftmost end of trace 20 near the bottom of pole piece 12.

The second and third trace layers are similarly interconnected by vias 58 (right end of traces 34 and 28), 60 (right end of traces 32 and 26), 62 (left end of traces 30 and 34), and 64 (left end of traces 28 and 32). This forms a solenoid coil around pole piece 12 which extends from the rightmost end of trace 30 near the top of pole piece 12 (as shown in FIG. 1A) to the leftmost end of trace 26 near the bottom of pole piece 12. The solenoid coil formed from the second and third trace layers is generally interior of the solenoid coil formed from the first and fourth trace layers.

The two solenoid coils are connected together by a via 66 which connects the leftmost end of trace 20, in the upper layer of traces, to the leftmost end of trace 26 in the second layer of traces. The result is a single solenoid coil having both a supply path and a return path for energizing current, with both paths being formed around a single pole piece 12. It is apparent that the new head does not require a coil to be formed around the other pole piece to provide a return current path, and so the new head may be particularly useful in connection with vertical recording methods. However, it is also apparent that another coil may be formed around the second pole piece (not shown) if vertical recording is not to be used.

Returning to FIG. 1A, the leftmost end of trace 14, and the rightmost end of trace 30 are connected, through vias 74 and 76, to bonding pads 70 and 72, respectively, which may be located on, for example, the uppermost (rightmost, as shown in FIG. 1C) surface of insulating layer 46. Conventional read/write signal generating and sensing circuitry (not shown) which generates writing current, or senses reading current generated in the head, is connected to the bonding pads in a known manner. The bonding pads may be located in any convenient location, but it is desirable that they be formed close to the ends of the traces to which they connect to minimize the resistance of the path between the line from the read/write signal generating and sensing circuitry.

The method of fabricating the new read/write head is as follows. Initially, the first insulating layer 36 is formed as a base for traces 14, 16 and 18, and the traces are formed thereon using any conventional lithographic and metal deposition technique. Then, the second insulating layer 38 is formed, using a conventional technique, and the upper surface (the surface to the right as shown in FIG. 1C) may be smoothed. The upper surface of layer 38 forms the base for traces 26, 28 and 30, which are then formed. The third insulating layer 40 is then formed, and the pole piece 12 is formed. The pole piece may be formed using similar lithographic techniques, although the pole piece may be somewhat thicker than the traces.

After the pole piece is formed, the fourth insulating layer 42 is formed and vias are formed to the second layers of traces. A metal layer is then deposited to form the third layer of traces which also serves to fill the vias with conductive material and thereby form the inner solenoid coil. At the same time, vias, which, as described below, will be used later to interconnect the first layer of traces and a fourth layer of traces may be formed and filled with conductive material. The method described in the aforementioned U.S. patent application Ser. No., entitled Microlithographic Technique Using Laser For Fabrication Of Electronic Components And The Like, may be used to form the vias.

After the third layer of traces have been formed and the interconnections have been formed through the vias between the second and third layers of traces, the fifth layer of insulating material, layer 44, is formed, and the vias formed to the first layer of traces. A metal layer is then deposited to form the fourth layer of traces, that is traces 20, 22 and 24 which also serves to fill the vias conductive material to provide the outer solenoid coil. Thereafter, the top insulating layer 46 is deposited.

The connections between the respective ends of traces 14 and 30 and the bonding pads 70 and 72 may be formed using the same method described above of interconnecting the ends of the respective traces. This may be done at any convenient point in the process.

As has been noted above, a head including a pole piece and conductors as described above constructed in accordance with the invention is useful in disk drives incorporating either horizontal or vertical recording techniques. This is a result of the fact that the solenoid coil formed around one pole piece, including both the interior and the exterior coil layers, provides both a supply path and a return path for the energizing current. Thus, the head does not require a second coil around the other pole piece to provide a return current path. Furthermore, the new method of making the head simplifies fabrication of the head.

It will be appreciated that a read/write head typically includes two pole pieces. In a head which is used in vertical recording, typically only one pole piece will be surrounded by a coil. However, if a head is to be used in longitudinal recording, one or both pole pieces may be surrounded by coils.

The foregoing description has been limited to a specific embodiment of this invention. It will be apparent, however, that variations and modifications may be made to the invention, with the attainment of some or all of the advantages of the invention. Therefore, it is the object of the appended claims to cover all such variations and modifications as come within the true spirit and scope of the invention.

What is claimed as new and desired to be secured by Letters Patent of the United States is:

1. In a magnetic storage device, a head comprising
   at least one pole piece disposed along a longitudinal axis and having a distal end adapted to be disposed adjacent to a storage medium of the magnetic storage device,
   a pair of electrically insulating layers, said pole piece being disposed therebetween, and
   a plurality of electrically conductive traces separated from said pole piece by said pair of insulating layers and selectively interconnected to form a solenoid around said pole piece, said solenoid having a pair of ends disposed adjacent to a proximal end of said pole piece and being continuous between said ends to provide a generally helical 2. The head of claim 1 wherein said pair of ends are adapted to be connected to a signal source for supplying the energizing current to and returning the energizing current from said solenoid.

3. The head of claim 2 wherein said plurality of traces are disposed at skewed directions with respect to the longitudinal axis on opposing surfaces of said pair of insulating layers and have a plurality of ends interconnected by vias through said insulating layers.

4. The head of claim 3 further comprising a pair of bonding pads adapted to be connected to the signal source, said pair of bonding pads being connected to the pair of ends of said solenoid by vias.

5. A magnetic head of the kind that includes at least one pole piece disposed along a longitudinal axis and having a distal end adapted to be disposed adjacent to a magnetic storage medium, comprising
   a pair of electrically insulating layers, said pole piece being disposed between said pair of layers,
   a first set of electrically conductive traces disposed at an angle with respect to the longitudinal axis and separated from said pole piece by one of said insulating layers,
   a second set of electrically conductive traces disposed at an angle with respect to the longitudinal axis and separated from said pole piece by the other one of said insulating layers, and
   traces of said first and second sets of traces being selectively interconnected through said pair of electrically insulating layers to form a solenoid around said pole piece, said solenoid having a pair of ends disposed adjacent to a proximal end of said pole piece and being continuous between said ends to provide a generally helical path for the flow or energizing current around said pole piece, a first portion of said generally helical path extending from said proximal end to a region of said distal end of said pole piece, and a second portion of said generally helical path returning from said region of said distal end to said proximal end of said pole piece.

6. The magnetic head of claim 5 wherein
   said first set of traces comprises a first plurality of generally planar traces disposed on a surface of said one of said insulating layers,
   said second set of traces comprises a second plurality of generally planar traces disposed on a surface of said other one of said insulating layers, and
   said first plurality of traces and said second plurality of traces being selectively interconnected by vias disposed through said pair of insulating layers to form said solenoid.

7. In a magnetic storage device, a head of the kind that includes at least one pole piece disposed along a longitudinal axis and having a distal end adapted to be disposed adjacent to a storage medium of the magnetic storage device, said head comprising
   a pair of electrically insulating layers, said pole piece being disposed therebetween,
   a first set of electrically conductive traces separated from said pole piece by a first one of said insulating layers,
   a second set of electrically conductive traces separated from said pole piece by a second one of said insulating layers, and
   traces of said first set of traces and traces of said second set of traces being selectively interconnected to form a pair of solenoids that are each electrically insulated from and disposed around said pole piece, each of said pair of solenoids extending from a proximal end of said pole piece to a region of said distal end, said solenoids being serially coupled together in said region of said distal end to provide a path for the round trip flow of energizing current from said proximal end to said distal end region, and back to said proximal end, all around said pole piece.

8. The head of claim 7 wherein:
   A. said first set of traces includes:
      i. a first plurality of generally parallel electrically conductive traces disposed on an insulating substrate in a first direction skewed with respect to the axis;
      ii. a third layer of insulating material disposed over said first plurality of traces; and
      iii. a second plurality of generally parallel electrically conductive traces disposed on said third insulating layer in a second direction skewed with respect to said axis, the second direction being different from said first direction, the traces of the second plurality of traces having a length that is generally shorter than the lengths of the traces of the first plurality of traces; and
   B. said second set of traces includes:
      i. a third plurality of generally parallel electrically conductive traces on disposed said second one of the pair of insulating layers in a direction skewed with respect to the axis and generally parallel to the first direction, the traces of the third plurality of traces having a length similar to the length of the traces of the second plurality of traces;
      ii. a fourth layer of insulating material disposed over said third plurality of traces; and
      iii. a fourth plurality of generally parallel electrically conductive traces disposed on said fourth insulating layer in a direction skewed with respect to the axis and generally parallel to the second direction, the traces of the fourth plurality of traces having a length similar to the length of the traces of the first plurality of traces.

9. The head of claim 8 wherein
   an end of at least one of the traces of the third plurality of traces overlays an end of a trace of the second plurality of traces,
   an end of at least one of the traces of the fourth plurality of traces overlays an end of a trace of the first plurality of traces, an end of a trace of the fourth plurality of traces overlays an end of a trace of the second plurality of traces, and each overlaying end being electrically coupled to a respective underlaying end thereby to form said pair of solenoids, a first one of the pair of solenoids comprising the traces of the first and fourth plurality of traces and a second one of the pair of solenoids comprising the traces of the second and third plurality of traces, with the second solenoid being generally interior of the first solenoid and the first and second coils being electrically coupled together to provide both said supply path and said return path for the energizing current.

10. The head of claims 1, 5, or 7 wherein the traces are selectively interconnected with vias produced by laser radiation.

11. The head of claims 1, 5, or 7 further comprising a second pole piece disposed adjacent to said at least one pole piece and insulated from said traces.

12. The head of claim 11 wherein a proximal end of said at least one pole piece is electrically coupled to a proximal end of said second pole piece.

13. The head of claim 12 wherein a distal end of said at least one pole piece is spaced closely to a distal end of said second pole piece relative to a spacing between said proximal end of said at least one pole piece and said proximal end of said second pole piece.

14. In a magnetic storage device, a head of the kind that includes a plurality of pole pieces, each disposed along a longitudinal axis and having a distal end adapted to be disposed adjacent to a storage medium and a proximal end opposite thereto, comprising a first pair of electrically insulating layers, a first one of the plurality of pole pieces being disposed between said first pair of layers, a first set of electrically conductive traces disposed at an angle with respect to the longitudinal axis and separated from said first pole piece by one of the insulating layers of said first pair, a second set of electrically conductive traces disposed at an angle with respect to the longitudinal axis and separated from said first pole piece by the other one of said first pair of insulating layers, a second pair of electrically insulating layers, a second one of the plurality of pole pieces being disposed between said second pair of layers, a third set of electrically conductive traces disposed at an angle with respect to the longitudinal axis and separated from said second pole piece by one of the insulating layers of said second pair, a fourth set of electrically conductive traces disposed at an angle with respect to the longitudinal axis and separated from said second pole piece by the other one of said second pair of insulating layers, an electrically insulating layer separating the second set of electrically conductive traces from the third set of electrically conductive traces, and traces of said first and second sets of traces being selectively interconnected and traces of said third and fourth sets of traces being selectively interconnected to form a plurality of solenoids, each of said solenoids: being disposed around one of said pole pieces; having a pair of ends disposed adjacent to the proximal end of said one pole piece; and, being continuous between said ends to provide a generally helical path for the flow of energizing current around said one pole piece, a first portion of said generally helical path extending from said proximal end to a region of the distal end of said one pole piece, and a second portion of said generally helical path returning from said region of said distal end to said proximal end of said one pole piece.

15. The head of claim 14 wherein said proximal end of said first pole piece is electrically coupled to said proximal end of said second pole piece.

16. The head of claim 15 wherein said distal end of said first pole piece is spaced closely to said distal end of said second pole piece relative to a spacing between said proximal end of said first pole piece and said proximal end of said second pole piece.

* * * * *

UNITED STATES PATENT AND TRADEMARK OFFICE
CERTIFICATE OF CORRECTION

PATENT NO.  : 4,972,287

DATED       : November 20, 1990

INVENTOR(S) : Shyam C. Das

It is certified that error appears in the above-identified patent and that said Letters Patent is hereby corrected as shown below:

Claim 1, line 14, after "helical" insert --path for the flow of energizing current around said pole piece, a first portion of said generally helical path extending from said proximal end to a region of said distal end of said pole piece, and a second portion of said generally helical path returning from said region of said distal end to said proximal end of said pole piece.--

Signed and Sealed this

Sixth Day of April, 1993

*Attest:*

STEPHEN G. KUNIN

*Attesting Officer*    Acting Commissioner of Patents and Trademarks